(12) United States Patent
Fukita et al.

(10) Patent No.: US 6,207,429 B1
(45) Date of Patent: Mar. 27, 2001

(54) METHOD FOR PRODUCING OPTICALLY ACTIVE CYCLOPROPANECARBOXYLIC ACID

(75) Inventors: Yoshikazu Fukita, Takarazuka; Takeshi Ishii, Yokohama; Hiroyuki Asako, Takarazuka, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/310,920

(22) Filed: May 13, 1999

(30) Foreign Application Priority Data

May 15, 1998 (JP) .................................................. 10-133270
May 15, 1998 (JP) .................................................. 10-133271
May 15, 1998 (JP) .................................................. 10-133272

(51) Int. Cl.$^7$ ...................................................... C12P 7/40
(52) U.S. Cl. ................................................ 435/136; 197/280
(58) Field of Search ....................................... 435/136, 280, 435/197

(56) References Cited

U.S. PATENT DOCUMENTS

| | | |
|---|---|---|
| 4,985,364 | 1/1991 | Hildebrand et al. . |
| 5,180,671 * | 1/1993 | Nishizawa et al. ................... 435/136 |
| 5,405,763 | 4/1995 | Nishizawa et al. . |

FOREIGN PATENT DOCUMENTS

| | | |
|---|---|---|
| 0164573A2 | 12/1985 | (EP) . |
| 0488999A1 | 6/1992 | (EP) . |
| 0497103A2 | 8/1992 | (EP) . |
| 4234991 | 8/1992 | (JP) . |

OTHER PUBLICATIONS

Patent Abstracts of Japan, 16:584 (Dec. 24, 1992).
Database WPI, Section Ch, Week 8847, Derwent Publications Ltd., XP002112036.
Satoshi Mitsuda et al., *Agriculture Biological Chemistry*, vol. 55(11), pp. 2865–2870, (1991).
Masako Nishizawa et al., *Bioscience Biotech Biochemistry*, vol. 57(4), pp. 594–598, (1993).
Masako Nishizawa et al., *Applied and Environmental Microbiology*, vol. 61, No. 9, pp. 3208–3215, (Sep. 1995).

\* cited by examiner

*Primary Examiner*—Herbert J. Lilling
(74) *Attorney, Agent, or Firm*—Birch, Stewart, Kolasch & Birch, LLP

(57) ABSTRACT

The objective of the present invention is to provide a method which makes it possible to produce (1R)-trans-2,2-dimethyl-3-(substituted vinyl)cyclopropane-1-carboxylic acid which is useful as the acid component of a pyrethroid ester in an industrially advantageous way.

This objective is achieved by a method for producing (1R)-trans-2,2-dimethyl-3-(substituted vinyl)cyclopropane-1-carboxylic acid, comprising reacting with 2,2-dimethyl-3-(substituted vinyl)cyclopropane-1-carboxylic acid esters represented by the general formula:

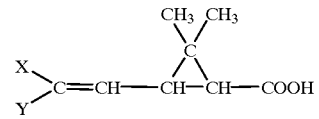

(wherein X is a hydrogen atom or a chlorine atom; Y is a methyl group when X is a hydrogen atom, whereas Y is a methyl group or a fluorine atom when X is a chlorine atom; and R is a $C_1$–$C_4$ alkyl group) an esterase capable of acting on and asymmetrically hydrolyzing said esters to (1R)-trans-2,2-dimethyl-3-(substituted vinyl)cyclopropane-1-carboxylic acid and esters of diastereomers thereof so that said esters are made resoluble into (1R)-trans-2,2-dimethyl-3-(substituted vinyl)cyclopropane-1-carboxylic acid and esters of diastereomers thereof; and isolating and recovering the (1R)-trans-2,2-dimethyl-3-(substituted vinyl) cyclopropane-1-carboxylic acid.

3 Claims, No Drawings

METHOD FOR PRODUCING OPTICALLY ACTIVE CYCLOPROPANECARBOXYLIC ACID

BACKGROUND OF THE INVENTION

1. Field of the Invention

The present invention relates to a method for producing (1R)-trans-2,2-dimethyl-3-(substituted vinyl)cyclopropane-1-carboxylic acid.

2. Description of the Related Art 2,2-dimethyl-3-(substituted vinyl)cyclopropane-1-carboxylic acids, which are represented by the general formula (1):

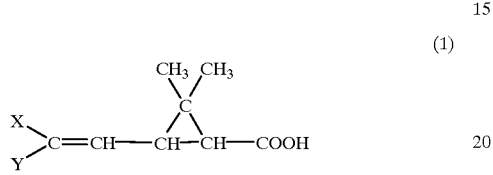

(wherein X is a hydrogen atom or a chlorine atom; and Y is a methyl group when X is a hydrogen atom, whereas Y is a methyl group or a fluorine atom when X is a chlorine atom) constitute the acid components of esters collectively called a synthetic pyrethroid having a highly effective insecticidal activity.

Since these cyclopropanecarboxylic acids have asymmetric carbon atoms in $C^1$ and $C^3$ positions thereof, there are 4 stereoisomers of cyclopropanecarboxylic acid. And, the pesticidal activity of the pyrethroid, whose acid component is one of these stereoisomers, varies according to target noxious insects, kinds of formulation, and the like. Accordingly, there is a demand for a method by which a desired specific stereoisomer of the cyclopropanecarboxylic acid is produced in an industrially advantageous way.

Under these circumstance, after intense studies for the establishment of an industrially advantageous method for producing (1R)-trans-2,2-dimethyl-3-(substituted vinyl) cyclopropane-1-carboxylic acid, the present inventors have achieved the invention based on finding that an esterase derived from a microorganism belonging to Genus Arthrobacter can act on 2,2-dimethyl-3-(substituted vinyl) cyclopropane-1-carboxylic acid esters represented by the general formula (2):

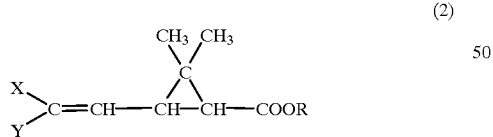

(wherein X is a hydrogen atom or a chlorine atom; Y is a methyl group when X is a hydrogen atom, whereas Y is a methyl group or a fluorine atom when X is a chlorine atom; and R is a $C_1$–$C_4$ alkyl group) so that the ester is asymmetrically hydrolyzed.

SUMMARY OF THE INVENTION

The present invention provides:

1. a method for producing (1R)-trans-2,2-dimethyl-3-(substituted vinyl)cyclopropane-1-carboxylic acid, comprising reacting with 2,2-dimethyl-3-(substituted vinyl)cyclopropane-1-carboxylic acid esters represented by the general formula (2) an esterase capable of acting on and asymmetrically hydrolyzing said esters to (1R)-trans-2,2-dimethyl-3-(substituted vinyl) cyclopropane-1-carboxylic acid and esters of diastereomers thereof so that said esters are made resoluble into (1R)-trans-2,2-dimethyl- 3-(substituted vinyl) cyclopropane-1-carboxylic acid and esters of diastereomers thereof; and isolating and recovering the (1R)-trans-2,2-dimethyl-3-(substituted vinyl)cyclopropane-1-carboxylic acid;

2. a method for producing (1R)-trans-2,2-dimethyl-3-(1-propenyl)cyclopropane-1-carboxylic acid, comprising reacting with 2,2-dimethyl-3-(1-propenyl) cyclopropane-1-carboxylic acid esters represented by the general formula (3):

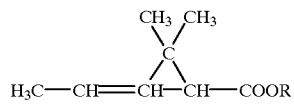

(wherein R is a $C_1$–$C_4$ alkyl group) an esterase capable of acting on and asymmetrically hydrolyzing said esters to (1R)-trans-2,2-dimethyl-3-(1-propenyl) cyclopropane-1-carboxylic acid and esters of diastereomers thereof so that said esters are made resoluble into (1R)-trans-2,2-dimethyl-3-(1-propenyl)cyclopropane-1-carboxylic acid and esters of diastereomers thereof; and isolating and recovering the (1R)-trans-2,2-dimethyl-3-(1-propenyl)cyclopropane-1-carboxylic acid;

3. a method for producing (1R)-trans-2,2-dimethyl-3-(2-chloro-1-propenyl)cyclopropane-1-carboxylic acid, comprising reacting with 2,2-dimethyl-3-(2-chloro-1-propenyl)cyclopropane-1-carboxylic acid esters represented by the general formula (4):

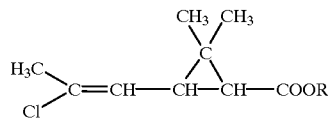

(wherein R is a $C_1$–$C_4$ alkyl group) an esterase capable of acting on and asymmetrically hydrolyzing said esters to (1R)-trans-2,2-dimethyl-3-(2-chloro-1-propenyl) cyclopropane-1-carboxylic acid and esters of diastereomers thereof so that said esters are made resoluble into (1R)-trans-2,2-dimethyl-3-(2-chloro-1-propenyl) cyclopropane-1-carboxylic acid and esters of diastereomers thereof; and isolating and recovering the (1R)-trans-2,2-dimethyl-3-(2-chloro-1-propenyl) cyclopropane-1-carboxylic acid;

4. a method for producing (1R)-trans-2,2-dimethyl-3-(2-chloro-2-fluorovinyl)cyclopropane-1-carboxylic acid, comprising reacting with 2,2-dimethyl-3-(2-chloro-2-fluorovinyl)cyclopropane-1-carboxylic acid esters represented by the general formula (5):

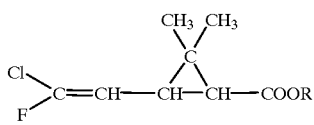

(wherein R is a $C_1$–$C_4$ alkyl group) an esterase capable of acting on and asymmetrically hydrolyzing said esters to (1R)-trans-2,2-dimethyl-3-(2-chloro-2-fluorovinyl) cyclopropane-1-carboxylic acid and esters of diastereomers thereof so that said esters are made resoluble into (1R)-trans-2,2-dimethyl-3-(2-chloro-2-fluorovinyl) cyclopropane-1-carboxylic acid and esters of diastereomers thereof; and isolating and recovering the (1R)-trans-2,2-dimethyl-3-(2-chloro-2-fluorovinyl) cyclopropane-1-carboxylic acid;

5. the method according to the above 1 to 4, wherein the esterase is an esterase derived from a microorganism belonging to Genus Arthrobacter; and 6. the method according to the above 1 to 4, wherein the esterase is an esterase derived from Arthrobacter SC-6-98-28 strain (FERM BP-3658).

There are geometrical isomers on a basis of the double bond of substituted vinyl group at a 3-position of cyclopropane ring which is comprised in the ester compounds represented by the general formulas 3 to 5 as described in the above 1 to 4, i.e. E-isomer and Z-isomer. Those geometrical isomer and a mixture thereof at any ratio may be used as a raw material in the present invention (2,2-dimethyl-3-(substituted vinyl) cyclopropane-1-carboxylic acid ester), and thus an end product corresponding to the raw material ((1R)-trans-2,2-dimethyl-3-(substituted vinyl) cyclopropane-1-carboxylic acid) can be obtained.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In an addition, throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

DETAILED DESCRIPTION OF THE PREFERRED EMBODIMENTS

The 2,2-dimethyl-3-(1-propenyl)cyclopropane-1-carboxylic acid esters represented by the general formula (3) for use as a raw material in the present invention may be produced by, for example, the method described in J. Chem. Soc. 1076 (1970). The carboxylic acid esters may be a methyl ester, an ethyl ester, a propyl ester, a butyl ester, and the like. In these esters, a methyl ester and an ethyl ester are preferable.

Further, the 2,2-dimethyl-3-(2-chloro-1-propenyl) cyclopropane-1-carboxylic acid esters represented by the general formula (4) for use as a raw material in the present invention may be produced by, for example, the method described in Chemical Listy 52, 688 (1958). The carboxylic acid esters may be a methyl ester, an ethyl ester, a propyl ester, a butyl ester, and the like. In these esters, a methyl ester and an ethyl ester are preferable.

Still further, the 2,2-dimethyl-3-(2-chloro-2-fluorovinyl) cyclopropane-1-carboxylic acid esters represented by the general formula (5) for use as a raw material in the present invention may be produced by, for example, the method described in Chemical Listy 52, 688 (1958). The carboxylic acid esters may be a methyl ester, an ethyl ester, a propyl ester, a butyl ester, and the like. In these esters, a methyl ester and an ethyl ester are preferable.

The esterase used in the present invention is one capable of acting on and asymmetrically hydrolyzing the 2,2-dimethyl-3-(1-propenyl)cyclopropane-1-carboxylic acid esters to (1R)-trans-2,2-dimethyl-3-(1-propenyl) cyclopropane-1-carboxylic acid and esters of diastereomers thereof or one capable of acting on and asymmetrically hydrolyzing the 2,2-dimethyl-3-(2-chloro-1-propenyl) cyclopropane-1-carboxylic acid esters to (1R)-trans-2,2-dimethyl-3-(2-chloro-1-propenyl)cyclopropane-1-carboxylic acid and ester of diastereomers thereof; or one capable of acting on and asymmetrically hydrolyzing the 2,2-dimethyl-3-(2-chloro-2-fluorovinyl)cyclopropane-1-carboxylic acid esters to (1R)-trans-2,2-dimethyl-3-(2-chloro-2-fluorovinyl)cyclopropane-1-carboxylic acid and esters of diastereomers thereof.

The esterase used in the present invention is, for example, an esterase which is derived from a microorganism belonging to Genus Arthrobacter and has the capability to cause the aforementioned asymmetric hydrolysis. For example, the esterase can be prepared from Arthrobacter SC-6-98-28 strain (FERM BP-3658: deposited in National Institute of Bioscience and Human-Technology Agency of Industrial science and Technology (Address: 1-3, Higashi 1 chome Tsukuba-shi Ibaraki-ken 305-0046, Japan) as an International Depositary Authority under the Budapest treaty). Preferably, the esterase can be prepared from a gene recombinant microorganism into which a gene encoding the esterase has been introduced and thus by which the esterase can be produced, and more specifically from, for example, the gene recombinant microorganism described in Japanese Patent Application Laid-Open (JP-A) No. 5-56,787.

In order to cause the above-mentioned microorganism to produce the esterase used in the present invention, the microorganism may be inoculated into a sterilized liquid culture medium according to conventional methods, and then the microorganism may be cultured at 20° C. to 40° C. for 1 day to 8 days in an aerobic condition. In addition, fed-batch culture, in which a culture medium is added during the growth, may be employed.

The composition of the culture medium used in the present invention is not particularly limited with the proviso that it is utilizable by the microorganism used in the present invention and may be a composition of the culture medium which is used for culturing ordinary microorganisms. Examples of carbon and nitrogen sources include glucose, glycerol, starch, dextrin, molasses, oils and fats, soybean powder, corn steep liquor, yeast extract, beef extract, hydrolysates of animal and plant proteins such as polypeptone, and the like. Examples of organic and inorganic salts include chlorides, sulfates, acetates, carbonates and phosphates of potassium, sodium, magnesium, calcium, iron, manganese, cobalt, zinc, and the like, more specifically potassium chloride, sodium chloride, cobalt chloride, magnesium sulfate, ferrous sulfate, manganese sulfate, zinc sulfate, copper sulfate, sodium acetate, calcium carbonate, sodium carbonate, monopotassium hydrogenphosphate, dipotassium hydrogenphosphate, monosodium hydrogenphosphate, and disodium hydrogenphosphate as well as ammonium salts such as ammonium sulfate, ammonium chloride and ammonium nitrate, urea, and the like. If necessary, it may be also possible to add a fatty acid ester or an ester compound represented by the general formula (3), (4), or (5) into the culture medium. In a case where a gene recombinant microorganism is used, a gene expression inducer such as isopropylthio-β-D-galactoside (IPTG) may be added at an appropriate point in the logarithmic growth phase of the microorganism.

According to the method of the present invention, the asymmetric hydrolysis reaction of 2,2-dimethyl-3-(substituted vinyl)cyclopropane-1-carboxylic acid esters represented by the general formula (2), i.e., 2,2-dimethyl-3-(1-propenyl)cyclopropane-1-carboxylic acid esters represented by the general formula (3), 2,2-dimethyl-3-(2-chloro-1-propenyl)cyclopropane-1-carboxylic acid esters represented by the general formula (4) or 2,2-dimethyl-3-(2-chloro-2-fluorovinyl)cyclopropane-1-carboxylic acid esters represented by the general formula (5) is performed by mixing the ester with the esterase. The esterase used in the present invention is in a form of, for example, an esterase-containing material such as a culture liquid in which the microorganism was cultured, a suspension of microorganism cells, a suspension of lysed microorganism cells, an extraction liquid of esterase, a concentrated esterase solution, or a treatment product thereof such as an aqueous solution containing a crude esterase or a purified esterase. If necessary, the microorganism or the esterase may be immobilized for use in the method of the present invention.

A reaction temperature is generally in the range of from 20° C. to 70° C., although the temperature varies depending on the optimal temperature for reaction and thermal stability of the esterase to be used. Since the stability of the esterase is liable to become inferior if the temperature is too high and the reaction rate becomes undesirably slower at a lower temperature, the temperature is preferably in the range of from 30 to 60° C. A pH value during the reaction is generally in the range of from 4 to 11 and the pH is desirably in the range of from 7 to 10, although the pH value varies depending on the optimal temperature for reaction and stability of the esterase to be used.

After the completion of the asymmetric hydrolysis reaction, the formed (1R)-trans-2,2-dimethyl-3-(substituted vinyl)cyclopropane-1-carboxylic acid, i.e., (1R)-trans-2,2-dimethyl-3-(1-propenyl)cyclopropane-1-carboxylic acid, (1R)-trans-2,2-dimethyl-3-(2-chloro-1-propenyl)cyclopropane-1-carboxylic acid or (1R)-trans-2,2-dimethyl-3-(2-chloro-2-fluorovinyl)cyclopropane-1-carboxylic acid, is recovered by the separation thereof from the unreacted ester. For the purpose of this recovery by separation, such processes as solvent extraction, column chromatography, fractional distillation, and the like, can be appropriately employed.

For example, a process for recovering the (1R)-trans-2,2-dimethyl-3-substituted vinyl)cyclopropane-1-carboxylic acid, i.e., (1R)-trans-2,2-dimethyl-3-(1-propenyl) cyclopropane-1-carboxylic acid, (1R)-trans-2,2-dimethyl-3-(2-chloro-1-propenyl)cyclopropane-1-carboxylic acid, or (1R)-trans-2,2-dimethyl-3-(2-chloro-2-fluorovinyl) cyclopropane-1-carboxylic acid, comprises the steps of: separating the unreacted ester by extracting the reaction solution with an organic solvent such as methyl isobutyl ketone, ethyl acetate, ether, toluene or the like, filtering the aqueous layer, adding an inorganic acid such as hydrochloric acid, sulfuric acid or the like, or an organic acid such as acetic acid or the like, to the aqueous solution so that pH thereof is shifted into an acidic region, extracting the aqueous solution with an organic solvent such as methyl isobutyl ketone, ethyl acetate, ether, toluene or the like, filtering the oil layer, and distilling off the organic solvent so as to obtain the product aimed at. The unreacted ester is subjected to a treatment such as racemization, and thereafter the ester can be utilized as a raw material for use in the method of the present invention. Alternatively, according to purposes, the unreacted ester is subjected to a treatment such as hydrolysis, and thereafter can be transformed into a pyrethroid ester.

EXAMPLES

The present invention is further explained below by way of examples. Therefore, the following examples are to be considered as illustrative and not restrictive.

Example 1

100 mL of a liquid culture medium (comprising 1L of water containing 5 g of glycerol, 6 g of yeast extract, 9 g of monopotassium hydrogenphosphate and 4 g of dipotassium hydrogenphosphate dissolved therein and adjusted to a pH value of 7.0) was placed in a 500 mL Erlenmeyer flask, the medium was sterilized, and ampicillin was added to a final concentration of 50 $\mu$g/mL. Then, one loopful amount of a slant culture of *Escherichia coli* into which an esterase gene derived from Arthrobacter SC-6-98-28 strain had been introduced as described in Example given below, was inoculated into the medium. The medium was then subjected to rotary shaking culture at 30° C. for 24 hours. Next, 1500 mL of a liquid culture medium (comprising 1L of water containing 15 g of glycerol, 25 g of yeast extract, 0.4 g of monopotassium hydrogenphosphate, 2 g of magnesium sulfate and 0.1 g of ferrous sulfate dissolved therein and adjusted to a pH value of 7.0) was placed in a small fermentor having a volume of 3L (MDL-model, manufactured by B. E. Marubishi Co., Ltd.) and then the medium was sterilized. Then 15 mL of the above-mentioned culture solution was inoculated into the medium. Then, culturing with airation and agitation was carried out at 30° C. and, in the middle of logarithmic growth phase of the microorganism (at about 13 hours after the start), IPTG (isopropylthio-β-D-galactoside) at a final concentration of 1 mM was added to the medium to induce the expression of the esterase. After that, to the medium was added a sterilized fresh culture medium, and the cultivation was further continued for 40 hours.

To 80 mL of a solution obtained from the culture solution after dilution (0.5 M carbonic acid-buffered solution, pH 9.5) was added 4 g of 2,2-dimethyl-3-(1-propenyl) cyclopropane-1-carboxylic acid methyl ester (1R-stereoisomer/1S-stereoisomer=50/50, trans-stereoisomer/cis-stereoisomer=98/2) and the solution was stirred at 45° C. for 20 hours while adjusting the pH value to 9.5. A part of the reaction solution taken out as a sample was acidified by adding hydrochloric acid and was then extracted with ethyl acetate. The extract, after the addition thereto of an internal standard substance (methyl cinnamate), was analyzed by gas chromatography (column: HR20-M, 0.53φ, 30 m, 1μ, manufactured by ULBON) to measure the hydrolysis ratio of the ester. As a result, the ratio was 46%.

Then, to the rest of the reaction solution was added toluene. After extraction and separation into layers, the toluene layer was removed. The aqueous layer obtained was filtered, and then was acidified by adding hydrochloric acid. To the aqueous solution was then added toluene for solvent extraction. The toluene layer thus obtained was concentrated and evaporated to obtain 1.5 g of 2,2-dimethyl-3-(1-propenyl)cyclopropane-1-carboxylic acid. The 2,2-dimethyl-3-(1-propenyl)cyclopropane-1-carboxylic acid thus obtained was analyzed by liquid chromatography (column: CHIRALCEL OD, 4.6φ×250 mm, manufactured by Daicel Ltd.) to measure the ratio of stereoisomers. The result was IR-trans-stereoisomer/1S-trans-stereoisomer/1R-cis-stereoisomer/1S-cis-stereoisomer=100/0/0/0.

Example 2

100 mL of a liquid culture medium (comprising 1L of water containing 5 g of glycerol, 6 g of yeast extract, 9 g of monopotassium hydrogenphosphate and 4 g of dipotassium hydrogenphosphate dissolved therein and adjusted to a pH value of 7.0) was placed in a 500 mL Erlenmeyer flask, the medium was sterilized, and ampicillin at a final concentration of 50 $\mu$g/mL was added. Then, one loopful amount of a slant culture of *Escherichia coli* into which an esterase gene derived from Arthrobacter SC-6-98-28 strain had been introduced as described in Example given below, was inoculated into the medium. The medium was then subjected to rotary shaking culture at 30° C. for 24 hours. Next, 1500 mL of a liquid culture medium (comprising 1L of water containing 15 g of glycerol, 25 g of yeast extract, 0.4 g of monopotassium hydrogenphosphate, 2 g of magnesium sulfate and 0.1 g of ferrous sulfate dissolved therein and adjusted to a pH value of 7.0) was placed in a small-fermentor having a volume of 3L (MDL-model, manufactured by B. E. Marubishi Co., Ltd.) and then the medium was sterilized. Then 15 mL of the above-mentioned culture solution was inoculated into the medium. Then, culturing with airation and agitation was carried out at 30° C. and, in the middle of logarithmic growth phase of the microorganism (at about 13 hours after the start), IPTG (isopropylthio-β-D-galactoside) at a final concentration of 1 mM was added to the medium to induce the expression of the esterase. After that, to the medium was added a sterilized fresh culture medium, and the cultivation was further continued for 40 hours.

To 80 mL of a solution obtained from the culture solution after dilution (0.5 M carbonic acid-buffered solution, pH 9.5) was added 4 g of 2,2-dimethyl-3-(2-chloro-1-propenyl)cyclopropane-1-carboxylic acid methyl ester (1R-stereoisomer/1S-stereoisomer=50/50, trans-stereoisomer/cis-stereoisomer=98/2) and the solution was stirred at 45° C. for 20 hours while adjusting the pH value to 9.5. A part of the reaction solution taken out as a sample was acidified by the adding hydrochloric acid and was then extracted with ethyl acetate. The extract, after the addition thereto of an internal standard substance (methyl cinnamate), was analyzed by gas chromatography (column: HR20-M, 0.53φ, 30 m, 1µ, manufactured by ULBON) to measure the hydrolysis ratio of the ester. As a result, the ratio was 47%.

Then, to the rest of the reaction solution was added toluene. After extraction and separation into layers, the toluene layer was removed. The aqueous layer obtained was filtered, and then was acidified by adding hydrochloric acid. To the aqueous solution was then added toluene for solvent extraction. The toluene layer thus obtained was concentrated and evaporated to obtain 1.6 g of 2,2-dimethyl-3-(2-chloro-1-propenyl)cyclopropane-1-carboxylic acid. The 2,2-dimethyl-3-(2-chloro-1-propenyl)cyclopropane-1-carboxylic acid thus obtained was analyzed by liquid chromatography (column: CHIRALCEL OD, 4.6φ×250 mm, manufactured by Daicel Ltd.) to measure the ratio of stereoisomers. The result was: 1R-trans-stereoisomer/1S-trans-stereoisomer/1R-cis-stereoisomer/1S-cis-stereoisomer 100/0/0/0.

Example 3

100 mL of a liquid culture medium (comprising 1L of water containing 5 g of glycerol, 6 g of yeast extract, 9 g of monopotassium hydrogenphosphate and 4 g of dipotassium hydrogenphosphate dissolved therein and adjusted to a pH value of 7.0) was placed in a 500 mL Erlenmeyer flask, the medium was sterilized, and ampicillin at a final concentration of 50 $\mu$g/mL was added. Then, one loopful amount of a slant culture of *Escherichia coli* into which an esterase gene derived from Arthrobacter SC-6-98-28 strain had been introduced as described in Example given below, was inoculated into the medium. The medium was then subjected to rotary shaking culture at 30° C. for 24 hours. Next, 1500 mL of a liquid culture medium (comprising 1L of water containing 15 g of glycerol, 25 g of yeast extract, 0.4 g of monopotassium hydrogenphosphate, 2 g of magnesium sulfate and 0.1 g of ferrous sulfate dissolved therein and adjusted to a pH value of 7.0) was placed in a small fermentor having a volume of 3L (MDL-model, manufactured by B. E. Marubishi Co., Ltd.) and then the medium was sterilized 15 mL of the above-mentioned culture solution was inoculated into the medium. Then, airation-agitation was carried out at 30° C. and, in the middle of logarithmic growth phase of the microorganism (at about 13 hours after the start), IPTG (isopropylthio-β-D-galactoside) at a final concentration of 1 mM was added to induce the expression of the esterase. After that, to the medium was added a sterilized fresh culture medium, and the cultivation was further continued for 40 hours.

To 80 mL of a solution obtained from the culture solution after dilution (0.5 M carbonic acid-buffered solution, pH 9.5) was added 4 g of 2,2-dimethyl-3-(2-chloro-2-fluorovinyl)cyclopropane-1-carboxylic acid methyl ester (1R-stereoisomer/1S-stereoisomer=50/50, trans-stereoisomer/cis-stereoisomer=98/2) and the solution was stirred at 45° C. for 20 hours while adjusting the pH value to 9.5. A part of the reaction solution taken out as a sample was acidified by adding hydrochloric acid and was then extracted with ethyl acetate. The extract, after the addition thereto of an internal standard substance (methyl cinnamate), was analyzed by gas chromatography (column: HR20-M, 0.53φ, 30 m, 1µ, manufactured by ULBON) to measure the hydrolysis ratio of the ester. As a result, the ratio was 48%.

Then, to the rest of the reaction solution was added toluene. After extraction and separation into layers, the toluene layer was removed. The aqueous layer obtained was filtered, and then was acidified by adding hydrochloric acid. To the aqueous solution was then added toluene for solvent extraction. The toluene layer thus obtained was concentrated and evaporated to obtain 1.6 g of 2,2-dimethyl-3-(2-chloro-2-fluorovinyl)cyclopropane-1-carboxylic acid. The 2,2-dimethyl-3-(2-chloro- 2-fluorovinyl)cyclopropane-1-carboxylic acid thus obtained was analyzed by liquid chromatography (column: CHIRALCEL OD, 4.6φ×250 mm, manufactured by Daicel Ltd.) to measure the ratio of stereoisomers. The result was 1R-trans-stereoisomer/1S-trans-stereoisomer/1R-cis-stereoisomer/1S-cis-stereoisomer=100/0/0/0.

Example 4

The *Escherichia coli*, into which an esterase gene derived from Arthrobacter SC-6-98-28 strain had been introduced, used in Examples 1 to 3, was prepared according to the method described in JP-A No. 5-56,787. The method was as follows. The plasmid pAGE-1, in which an esterase gene derived from Arthrobacter SC-6-98-28 strain described in JP-A No. 5-56,787 is contained, was digested with restriction enzymes Nsp(7524)V and Hind III to cut out DNA fragments containing the translational region of the esterase gene. Then, as described in JP-A No. 5-56,787, the fragments were ligated to DNA fragments, which were synthesized to change esterase gene initiation codon and DNA sequence in the vicinity thereof, and a restriction enzyme-digestion product which was obtained by digesting an lac promoter-containing expression vector pUC118 (manufactured by Takara Shuzo Co., Ltd.) with restriction enzymes Bam III and Hind III. In this way, an expression plasmid having at a site downstream from the lac promoter the Arthrobacter SC-6-98-28 strain-derived esterase gene for use in *Escherichia coli* was prepared. The expression plasmid thus prepared was introduced into *Escherichia coli* (Strain JM105).

As stated above, the present invention makes it possible to produce (1R)-trans-2,2-dimethyl-3-(substituted vinyl) cyclopropane-1-carboxylic acid represented by the general formula (1) which is useful as the acid component of a pyrethroid ester in an industrially advantageous way.

What is claimed is:

1. A method for producing (1R)-trans-2,2-dimethyl-3-(substituted vinyl)cyclopropane-1-carboxylic acid, comprising reacting 2,2-dimethyl-3-(substituted vinyl)cyclopropane-1-carboxylic acid esters represented by the general formula:

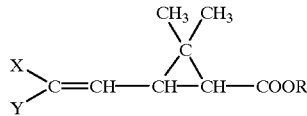

wherein X is a hydrogen atom or a chlorine atom; Y is a methyl group when X is a hydrogen atom, whereas Y is a fluorine atom when X is a chlorine atom; and R is a $C_1$-$C_4$ alkyl group with an esterase derived from Arthrobacter strain FERM BP-3658 capable of acting on and asymmetrically hydrolyzing said esters to (1R)-trans-2,2-dimethyl-3-(substituted vinyl)cyclopropane-1-carboxylic acid and esters of diastereomers thereof so that said esters are made resoluble into (1R)-trans-2,2-dimethyl-3-(substituted vinyl)cyclopropane-1-carboxylic acid and esters of diastereomers thereof; and isolating and recovering the (1R)-trans-2,2-dimethyl-3-(substituted vinyl)cyclopropane-1-carboxylic acid.

2. A method for producing (1R)-trans-2,2-dimethyl-3-(1-propenyl)cyclopropane-1-carboxylic acid, comprising reacting 2,2-dimethyl-3-(1-propenyl)cyclopropane-1-carboxylic acid esters represented by the general formula:

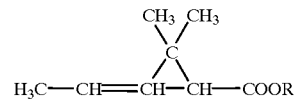

wherein R is a $C_1$-$C_4$ alkyl group with an esterase derived from Arthrobacter strain FERM BP-3658 capable of acting on and asymmetrically hydrolyzing said esters to (1R)-trans-2,2-dimethyl-3-(1-propenyl)cyclopropane-1-carboxylic acid and esters of diastereomers thereof so that said esters are made resoluble into (1R)-trans-2,2-dimethyl-3-(1-propenyl) cyclopropane-1-carboxylic acid and esters of diastereomers thereof; and isolating and recovering the (1R)-trans-2,2-dimethyl-3-(1-propenyl)cyclopropane-1-carboxylic acid.

3. A method for producing (1R)-trans-2,2-dimethyl-3-(2-chloro-2-fluorovinyl)cyclopropane-1-carboxylic acid, comprising reacting 2,2-dimethyl-3-(2-chloro- 2-fluorovinyl) cyclopropane-1-carboxylic acid esters represented by the general formula:

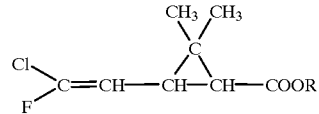

wherein R is a $C_1$-$C_4$ alkyl group, with an esterase derived from Arthrobacter strain FERM BP-3658 capable of acting on and asymmetrically hydrolyzing said esters to (1R)-trans-2,2-dimethyl-3-(2-chlor-2-fluorovinyl)cyclopropane-1-carboxylic acid and esters of diastereomers thereof so that said esters are made resoluble into (1R)-trans-2,2-dimethyl-3-(2-chloro-2-fluorovinyl)cyclopropane-1-carboxylic acid and esters of diastereomers thereof; and isolating and recovering the (1R)-trans-2,2-dimethyl-3-(2-chloro-2-fluorovinyl) cyclopropane-1-carboxylic acid.

* * * * *